United States Patent
Van der Krieken et al.

(10) Patent No.: US 6,242,381 B1
(45) Date of Patent: Jun. 5, 2001

(54) INFLUENCING THE ACTIVITY OF PLANT GROWTH REGULATORS

(75) Inventors: Wilhelmus Maria Van der Krieken, Wageningen; Gerrit Smit, Ede, both of (NL)

(73) Assignee: Instituut voor Agrobiologisch en bodemvruchtbaarheidsonderzoek (NL)

( * ) Notice: Subject to any disclaimer, the term of this patent is extended or adjusted under 35 U.S.C. 154(b) by 0 days.

(21) Appl. No.: 08/981,110

(22) PCT Filed: Jun. 24, 1996

(86) PCT No.: PCT/EP96/02789

§ 371 Date: Mar. 13, 1998

§ 102(e) Date: Mar. 13, 1998

(87) PCT Pub. No.: WO97/00614

PCT Pub. Date: Jan. 9, 1997

(30) Foreign Application Priority Data

Jun. 22, 1995 (EP) .................................................. 95201686
Nov. 9, 1995 (NL) .................................................. 1001620

(51) Int. Cl.[7] .......................... A01N 25/00; A01N 25/28; A01N 61/00; A01N 47/12

(52) U.S. Cl. ....................... 504/116.1; 504/189; 504/302; 504/359

(58) Field of Search ..................................... 504/116, 359, 504/116.1, 189, 302

(56) References Cited

U.S. PATENT DOCUMENTS

| | | | |
|---|---|---|---|
| 3,890,299 | 6/1975 | Fox et al. ..................... | 260/211.5 R |
| 4,169,717 | 10/1979 | Ashmead ................................. | 71/89 |
| 4,291,497 | 9/1981 | Manankov ................................ | 47/58 |
| 4,380,626 | 4/1983 | Szejtli et al. ......................... | 536/103 |

FOREIGN PATENT DOCUMENTS

| | | | |
|---|---|---|---|
| 124409 | 2/1977 | (DE) | ................................ A01N/5/00 |
| 128544 | 11/1977 | (DE) | ............................. C07C/69/74 |
| 0272002 | 6/1988 | (EP) | ............................. A01N/63/00 |
| 79/00838 | 10/1979 | (WO) | ............................. A01N/5/00 |
| 95/27395 | 10/1995 | (WO) | ............................. A01N/25/10 |
| 95/31970 | 11/1995 | (WO) | ............................. A61K/9/127 |

OTHER PUBLICATIONS

Database WPI, Section Ch. Week 9403 Derwent Publication Ltd., London, GB; AN 94–022784 XP002004912& JP,A,05 331 016 (Dainippon Pharm Co., Ltd.), Dec. 14, 1993.

Database WPI, Section Ch. Week 9019 Derwent Publications Ltd., London, GB; AN 90–144844, XP002004913 & JP,A,02 092 220 (Japan Tabacco & Salt Pub), Apr. 3, 1990.

*Primary Examiner*—S. Mark Clardy
(74) *Attorney, Agent, or Firm*—Webb Ziesenheim Logsdon Orkin & Hanson, P.C.

(57) ABSTRACT

The invention relates to methods for increasing and/or prolonging in vivo or in vitro activity of plant growth regulators (PGRs), comprising of locally increasing the concentration of active plant growth regulators in a plant and/or plant part(s) and/or increasing the sensitivity of the plant and/or plant part(s) to the activity of the plant growth regulators. The local increase can for instance take place by administering the PGRs in capsules. The increase in the sensitivity can be brought about by administering elicitors or means which result in the formation of elicitors. By adding both elicitors and (modified, e.g. slow-release) PGRs the induced response can be timed.

15 Claims, No Drawings

INFLUENCING THE ACTIVITY OF PLANT GROWTH REGULATORS

The present invention relates to a method for increasing and/or prolonging the activity of plant growth regulators (PGRs) after in vivo or in vitro application.

Plant growth regulators are natural or synthetic compounds which play a part in a large number of growth, development and metabolic processes in the plant. The best known plant growth regulator are auxins, gibberellins, cytokinins, ethylene, abscisic acid and jasmonic acid.

By administering such PGRs it is possible to intervene in different physiological processes, such as root formation in tissue culture, in cuttings and embryos, the maturing of fruit or vegetables, senescence (ageing) of flowers and yellowing of leaves and the like, germination of seed, induction of flowers, fruits, buds and the like.

In addition to influencing these natural processes, effects which do not occur naturally can also be achieved, for instance the development of seedless fruit, larger fruits, regulating of the harvest by preventing the fall of fruits, thinning out of fruits in fruit trees, a regulated growth retarding of trees and branches or shoots and young plants, regulated branch formation, induction of shoot formation for instance in barley in order to produce malt, an increase in the sensitivity to herbicides, inhibiting the coarsening of the skin of fruits such as apples, bananas, production of somatic embryos and the like.

Different PGRs can play a part in influencing these and other processes in plants or parts thereof. Although it would seem evident that such influencing could be realized by increasing the concentration of a PGR or by applying a number of PGRs, this is found in practice not to be the case.

Most PGRs are degraded without achieving their final purpose after being taken up into the plant. In addition, high concentrations of PGR in particular have an effect on any random cell, which can be disadvantageous if a very localized activity is sought after.

In addition, problems also occur with particular PGRs in the administering thereof. PGRs are generally added to water which is supplied to the plant by watering, sprinkling and the like. The insolubility of some PGRs in water results in poor absorption into the plant.

It is the object of the present invention to increase and/or prolong and/or time the activity of PGRs in vivo or in vitro in order to enable a specific influencing of physiological and other processes at the right moment and place.

This is achieved by the invention by locally increasing the concentration of active plant growth regulators in a plant and/or plant part(s) and/or increasing the sensitivity of the plant and/or plant part(s) to the activity of the plant growth regulators. The combination of these can be used to time the availability and/or action of the plant growth regulators as will be explained hereinbelow.

The increase in the concentration of active plant growth regulators in the plant and/or plant part(s) is for instance achieved by administering the PGRs in encapsulated form to the plant and/or plant part(s). Such a capsule can be a liposome or micelle-like structure. Although liposomes are known per se, the use thereof to administer substances to plants is new.

It has been found according to the invention that by administering the PGRs in a liposome or micelle a pool of (potentially active) PGRs is formed in the plant tissue. Through differences in lipophilicity and by varying the size of the micelles and liposomes the transport in the plant can be regulated. In addition, the liposomes and micelles can optionally be sent to a specific tissue or organ by including in the membrane so-called "targeting" molecules. The localization of the activity is hereby enhanced.

The stability of the liposomes, which consist of a double layer of phospholipids, can be regulated since this greatly depends on the composition of the lipid membrane. Substances can thus be included in the membrane which are degraded in the plant. In this way the liposome will begin to leak and releases its contents. The stability can also be influenced by enzymes, such as esterases, lipases and phospholipases, which are present in the plant. Conversely, the stability can be increased by addition of sterols or through the use of saturated phospholipids. Further, addition of surface active agents (detergents) can trigger the release of the contents. In such a case the liposomes or micelles are first administered to the plant and later a detergent, whereby the liposomes or micelles dissolve and release their contents.

Micelles consist of molecules with a polar water-soluble and a non-polar fat-soluble side and are very suitable for dissolving non-polar PGRs in a polar medium such as water. When non-polar PGRs are mixed with the micelle-forming molecules, the non-polar ends will encapsulate the PGR, whereafter the polar ends will dissolve the whole in the surrounding medium. It is likewise possible to first dissolve the PGR in oil and then to introduce the small oil droplets into micelles. The mixture of micelles and oil with PGRs can be mixed with water. The thus obtained solution can be carried into the plant by sprinkling or by administering to the roots or the severed surface of the stem.

In another embodiment the PGRs can be chemically modified by linking one or more carrier molecules thereto in covalent manner. Such carrier molecules can have different functions.

There are therefore carrier molecules which have a transporting function. It is known that particular transport systems are present inside a plant. Carbohydrate molecules are for instance transported to young developing tissue, flowers or roots. By linking a PGR to such a carrier molecule, transport to a desired tissue can be effected.

The transportable compounds can be chosen for instance from the group which consists of carbohydrates, such as sucrose, glucose, sorbitol, sterols, terpenes, phosphorylated hydrocarbons and the like.

Another type of carrier molecule has polarity-influencing properties. This is important for the absorption of the PGRS. When a PGR has to be absorbed through the leaf, it must first pass through the wax layer on the leaf. This is facilitated when the PGR is linked to a non-polar, fat-soluble substance. Conversely, absorption via the severed stem proceeds better when the PGR is polar, water-soluble and preferably negatively charged. The negative charge is advantageous because positively charged compounds bind easily to the vascular tissue of the stem.

PGRs are nearly all acidic compounds and therefore polar. By linking a PGR to a carrier, a spacer or a second PGR molecule (optionally of the same type) the polarity disappears because the charged group is used for linking. Such linking can proceed via ester or peptide bonds. In the case of an alkaline PGR an acidic carrier or spacer can be used. If it is wished however to make the PGR polar, this can for instance take place by linking to a sugar via an ester bond or by making a sulphonate of the PGR. Such compounds have more charge than the PGR itself and therefore make it even more polar.

The activity of PGRs is often brought to an end in the plant by degrading processes. Because the carrier molecule with the group which the (degradation) metabolism affects is bound to the PGR, a PGR compound is created which is protected against degradation and the lifespan of the PGR in the plant can be prolonged. It is however important here that the protective group either does not deactivate the PGR or that the binding of the protective group is reversible, so that the PGR which is deactivated by binding of the group regains its activity after splicing from the group. Such a protective compound is preferably linked to the site in the PGR which is involved in metabolic reactions.

The carrier molecules can be linked directly or with interposing of one or more spacers to the PGRS, for instance by means of a covalent ester, ether or amide bond. The choice of the spacer and the ambient conditions determine the release speed of free PGR from the carrier molecule.

Another way of protecting a PGR against degradation is the use of a spacer molecule which is arranged between the carrier molecule and the PGR. Such a spacer ensures that the release speed of the PGR can be influenced. Enzymes, such as esterases, peptidases and the like-have a different affinity for the different spacer molecules.

In a specific embodiment the compounds which protect against degradation also serve as spacer molecules and are for instance chosen from the group consisting of succinic acid, malonic acid, diaminoalkanes, such as 1,2-diaminoethane, 1,4-diaminobutane, 1,6-diaminohexane and the like.

It is also possible to offer a hormone precursor, which is converted into an active hormone by metabolic processes. Indole-3-hexanoic acid (I-H-A) is converted by two beta-oxidation steps (the enzymes therefor are present in the plant) into the auxin indole-3-acetic acid (I-A-A). I-H-A is thus a special form of a slow-release source. I-H-A was found to be thirty times more active than I-A-A in root induction in apple and rose.

The activity of PGRs can be further influenced by administering them together with so-called "elicitors". The combination of the two is especially important as tissue sensitivity has to be developed in time. The responding tissue has first to dedifferentiate, after which the tissue acquires competence to respond to PGR's. "Elicitors" are substances which results in a defensive response in the plant and/or plant part(s) and cause this dedifferentiation. Their natural role in plants, in addition to inducing the production of phytoalexins, is to regulate the recovery of plants after damage or severe stress.

Cell compartments (vacuoles, vesicles, plastids) in which catabolic enzymes (e.g. peroxidases, phospholipases, phosphatases) are situated are damaged by injury. These enzymes degrade cell structures whereby elicitors are formed. Peroxidases can degrade the cell membrane so that oligosaccharides, such as sulphonated lignin fragments, and lignin monomers, such as tannic acid, or ferulic acid is formed. Phospholipases degrade the cell membrane to fatty acids such as oleic acid, linoleic acid and linolenic acid. Formed herefrom are for instance jasmonic acid (from linolenic acid) and nonanoic acid (from oleic acid). Through phosphatases uridine can be formed from uridine monophosphate (derived from ribonucleic acid). All these substances are found to have an elicitor activity.

Elicitors which do not originate directly from the degradation of cell structures can also be used to increase tissue sensitivity, such as fusicoccin, pythium extract, cellulase/pectinase, 4-acetamidophenol, lipo (chito) oligosaccharides/glutathione, etc.. In addition, means can be used which result in the formation of elicitors. Such means are for instance UV-B (non-chemical induction of tissue sensitivity to PGRs), ozone, etc.. Intermediaries from the phytoalexin biosynthesis are also suitable. These intermediaries are for instance anthocyans, sterols, etc..

When a shoot is cut off a plant elicitors will be formed at the position of the wound. In the top of the shoot, in which young leaves and meristem are situated, auxins are also produced, which are transported to the wound via the usual polar auxin transport system. auxins and elicitors thus collect at the wound. The latter increase the tissue competence, whereby the tissue develops the ability to respond to inducing factors, while the auxins induce root formation. A rooted shoot is thus formed.

A similar mechanism occurs in the case of cytokinins. They move naturally from their synthesis position in the roots to the top of the plant. It has now been found that when the top is broken off elicitors are formed which make the tissue in the vicinity of the wound more sensitive to the activity of the cytokinins. In this way new shoots are formed.

This mechanism also occurs in auxin/cytokine-induced flower bud formation on thin layer tissue culture strips cut from flower stems of tobacco. (see table).

It has now been found according to the invention that the activity of the elicitors relates not only to induction of defence mechanisms (production phyto-alexins), but also to induction of tissue competence/sensitivity to PGRs. The activity of the elicitors is not specifically directed at root, flower bud or shoot but very generally influences the sensitivity of the tissue to other factors. Based on this principle elicitors can be used to boost the activity of PGRs.

It has been found that such elicitors can boost and/or prolong the activity of PGRs. This is also the case with induction of somatic embryogenesis and the use of herbicides.

Thus, elicitors may be used to build up sensitivity of the plant tissue for PGRs. In turn the PGRs trigger the desired response. In most situations it is desirable to develop tissue sensitivity in time. The responding tissue has first to dedifferentiate, after which the tissue acquires competence to respond to PGRs. An early availability of the PGRs is then not required or even less desirable because the majority of the PGR(s) administered can be degraded by the plant's metabolic system before the PGR(s) gets a chance to perform its (their) function. A later administration or the use of a slow-release form of the PGR(s) is then the solution. A preferred embodiment of the invention is therefore to combine (chemically modified) PGRs and elicitors.

For example, the synergistic effect of IHA and other chemically modified PGRs and elicitors on root formation is not only that the rate of inactivation by the metabolism decreases but also that the active auxin (IAA) is released later in time. This is very important because the tissue can not respond immediately to the PGRs. It first has to become sensitive for the PGRs, which sensitivity is enhanced by the action of elicitors. Development of sensitivity for auxins in e.g. apple or tobacco takes about 1 to 1.5 days. During this period however, commercially available auxins are largely inactivated by the metabolic action of the plant.

It was found that application of elicitors is most effective when they are applied prior to the addition of a PGR. Incubation in vivo of apple tissue during one day on medium containing pythium extract (which has a synergistic effect on rooting as compared to auxin alone) followed by an incubation of one day on medium with normal auxin resulted in a two-fold increase as compared with an experiment in which both pythium extract and auxin were applied simultanously for one day. Addition of a chemically modified slow-release auxin together with an elicitor has the same effect as application of the elicitor before the hormone, because the elicitior starts immediately to induce sensitivity and the release source dissociates the PGR after the tissue has acquired sensitivity.

Similarly it was found that a chemically modified auxin (e.g. IHA) in combination with an elicitor (e.g. nonanoic acid) does improve the rooting of plant tissue, recalcitrant (difficult to root) to rooting, than the IHA alone, which in itself induces already better rooting than IBA alone. An experiment performed to illustrate this was the rooting of very recalcitrant scions of apple (c.v. elstar). Using standard rooting powder containing 2% IBA (w/w) in talc=30%) the maximum rooting frequency obtained was 30%; using a rooting powder containing 1% IHA (w/w) and 0.5% nonanoic acid (w/w) in talc, the maximum rooting frequency increased to 93%! In order to understand the fact that IHA is such a good PGR it was checked whether indeed IBA (a natural occuring auxin) is the compound which induces the rooting. Surprisingly it was found that not IBA but IAA seems to be the active component and therefore also IBA, similar to IHA (which first transforms to IBA), becomes active via conversion into IAA, thus IBA is in fact also a natural slow release source. Indeed combination of IBA with an elicitor also resulted in a very strong increase in the rooting response as compared to application of IBA or IAA alone.

Furthermore, it was found that elicitors in combination with PGRs can also be used to improve the frequency of transformation/regeneration and the formation of plants out of cells or protoplasts. It was also observed that tissue explants of rose when treated with IBA (normal addition) or IHA, respectively, formed about 50 times more shoots (2 shoots versus 100 per 20 tissue explants) in the latter case.

In the studies for new applications of PGR's and/or elicitors, which were performed within the framework of the present invention, several new and unexpected observations were made. For example, it was found that elicitors do influence microspore embryogenesis. Applying nonanoic acid in combination with a classical chemical PGR like colchicine in the embryogenesis of *Brassica napens* an increase of 125% in microspore embryogenesis was obtained. Furthermore, the inventors established that elicitors do cause a statistically significant growth retardation of all tissues, as can be illustrated for rose shoots. This effect was enhanced by PGR(s), in casu antigibberelins, i.e. paclobutrasol. Also, elicitors were found to improve the grafting of scions on rootstocks, which effect might be enhanced by auxins. Finally the observation was made that when tissue explants of rose were treated with respectively IBA (normal addition) or IHA, in the last case about 50 times more shoots were formed (2 shoots versus 100 per 20 tissue explants).

In addition to the use of elicitors per se, plants can also be transformed with genes which code for elicitors. The sensitivity of the plant to the PGRs hereby increases. The genes which code for the elicitors can be under the regulation of different types of promoters. Such promoters are preferably inducible by for instance a cold shock, heat shock, wounding or chemicals, such as tetracycline. Tobacco plants in which NOD genes of *Rhizobia* were expressed (coding for lipo (chito) oligosaccharides; see table) formed many more shoots than wildtype plants. This indicates an increased cytokinin sensitivity of the tissue.

On the basis of the general principle a skilled person will be capable of devising different embodiments, all falling within the scope of the invention. The general principle of the invention consists of optimizing the activity of PGRs by increasing the quantity of active PGRs at desired locations in the plant and/or by making the plant more sensitive to the activity thereof. The increase in the active quantity can be achieved by using chemically modified and/or encapsulated PGRs. Sensitizing is achieved by exogenous or endogenous elicitors. All conceivable combinations of chemical modification, encapsulation and elicitors of course fall within the scope of the invention. Elicitors can therefore also be chemically modified or incorporated in liposomes or micelles, alone or in combination with the PGRs. They can also be linked chemically to one or more PGRs, optionally with interposing of a spacer.

The preferred combination of the invention is a combination of elicitors with chemically modified PGRs. The combination leads to optimal activity because the elicitor confers tissue sensitivity after which the PGR, that has regained activity after release from the carrier or spacer molecule, can exert maximum activity.

The invention further relates to compositions for increasing and/or prolonging the in vivo or in vitro activity of plant growth regulators (PGRs), comprising an aqueous solution of capsules, such as liposomes, micelles etc., containing at least one plant growth regulator. Elicitors and/or means which result in the release of elicitors can optionally also be included in the capsules. Such means are for instance enzymes, intermediaries from the phytoalexin biosynthesis etc..

The invention also provides chemically modified compounds, consisting of at least one PGR which is linked to at least one carrier molecule.

According to another aspect of the invention vegetatively multiplied plants, cuttings or somatic embryos are provided, which are produced by using one or more of the methods and/or compositions and/or chemically modified compounds according to the invention.

Also falling within the scope the invention are physiologically manipulated flowers, plants or somatic embryos produced by using one or more of the methods and/or compositions and/or chemically modified compounds according to the invention. Physiologically manipulated flowers, plants or somatic embryos are flowers, plants or embryos which display properties other than natural ones.

In addition, the invention provides genetically modified flowers, plants or somatic embryos produced by transformation with genes which code for elicitors and/or for means which induce the formation of elicitors.

Another aspect of the invention relates to the use of elicitors, or means which result in the production thereof, to increase the sensitivity of a plant and/or plant part(s) to the activity of PGRs and the use of chemically modified compounds to increase the concentration of active PGRs in a plant and/or plant part(s).

The present invention will be further illustrated with reference to the accompanying examples, which are only given by way of illustration and are not intended to limit the invention in any way whatever.

EXAMPLES

Example 1

Introduction of a dye into plant tissue via liposomes and micelles

The technique for producing liposomes is generally known per se. For a survey reference is made to Chemistry & Physics of Lipids 64, 35–43 (1993).

The diameter of liposomes can vary considerably. The so-called Large Unilamellar Vesicles Through Extrusion Techniques (LUVETs) have for instance a diameter of 40 to 500 nm. The Multilamellar Vesicles (MLVs) have a diameter of 1 tot 10 μm and the Small Unilamellar Vesicles (SUVs) a diameter of about 20 to 40 nm.

In this example use was made of LUVETs. A fluorescent dye (fluorescein) was used as test compound. The LUVETs, which form a suspension in water, were administered to the cut flowers rose, alstroemeria and carnation. After 6 hours the fluorescent dye was detectable in leaf and flower tissue of these plants, with the naked eye or UV-light. This proves that liposomes can be used for the release of substances in plant tissue and in analogous manner to build up a pool of PGRs in the plant.

Furthermore, application of radioactively labeled liposomes (to lily) showed that the liposomes were transported through the stem tissue.

Example 2

Protection of PGRs against metabolic degradation by means of a spacer

In this example succinic acid was used as spacer in the synthesis of a compound of an anti-ethylene PGR compound (called A-S-A). Anti-ethylenes are involved amongst other things in retarding the ageing of the plant. By preventing metabolic degradation of these anti-ethylenes the activity thereof can be prolonged or boosted.

The compound A-S-A consists of two aminoisobutyric acid (AIB) molecules, which are linked to both ends of succinic acid.

The compound was obtained by dissolving 5 mM aminoisobutyric acid methylether (prepared according to the literature (J. Chem. Soc. (Perkin Transactions I) (1979) p. 2138) and 2.5 mM succinic acid in 20 ml dichloro-methane. The solution was cooled to $-5°$ C. 2.5 mM dicyclohexylcarbodiimide was added to this solution and the mixture was stirred for two hours at $-5°$ C. and thereafter for 24 hours at room temperature. The precipitate was filtered off and the clear dichloromethane solution was washed with water, a 10% citric acid solution and a saturated sodium chloride solution. After evaporation of the dichloromethane the compound A-S-A was obtained.

When the A-S-A in water (concentration $5 \times 10^5$ to $10^{-3}$ M) was administered to cut flowers (carnations) it was found to be 50 times more active in retarding the ageing of the flowers than non-modified AIB.

Example 3

The use of a transport molecule

Sorbitol is a transportable carbohydrate in Rosaceae plants (except roses). Two compounds were synthesized which can be used to boost the activity of auxin. The first compound S-I-A consists of an indolebutyric acid molecule linked to a sorbitol. The second compound (4-S-N-A) consists of 4 naphthaleneacetic acid linked to a sorbitol.

S-I-A was prepared by suspending 2.4 mM indole butyric acid and 2.9 mM sorbitol in 25 ml dichloromethane. After the solution had been cooled to $0°$ C., 2.5 mM dicyclohexylcarbodiimide and 0.25 mM 4-pyrrolidino pyridine were added. This solution was stirred for 24 hours at ambient temperature. The precipitate was filtered off and the clear dichloromethane solution was washed with water, 1 N HCl solution and a saturated sodium chloride solution. After evaporation of the solvent S-I-A was obtained.

4-S-N-A was prepared in substantially the same manner as S-I-A using 12 mM 1-naphthaleneacetic acid, 3 mM sorbitol, 13 mM dicyclohexylcarbodiimide and 1.2 mM 4-pyrrolidinopyridine and 75 ml dichloromethane. S-I-A was mixed with talc (0.1% S-I-A) used as rooting powder and was found to be capable of inducing root formation in apple, rose and tobacco.

An alternative to an auxin rooting powder is an auxin rooting spray. 4-S-N-A is very non-polar and induced root formation when administered by spraying via the leaves of apple shoots.

Example 4

The use of a transport molecule and a spacer

In order to test glucose as carrier molecule for transport and acetate as spacer, a glucose-acetate-amino-oxyacetic acid (G-A-A) compound was synthesized.

For this purpose D-glucose was converted to its di-O-isopropylidene derivative according to standard procedures. 3 mM of this compound was dissolved in 25 ml chloroform together with 0.6 ml pyridine. This solution was cooled to $0°$ C. 10 ml 4mM chloroacetyl chloride in chloroform was added dropwise to this solution during continuous stirring. The chloroform solution was thereafter washed with 1 N HCl and saturated sodium chloride. Evaporation of the solvent gave the chloroacetyl glucoside.

1 mM of the chloroacetyl glucoside was dissolved in 15 ml dimethylformamide (DMF) with 1 ml water, 1 mM aminooxyacetic acid together with 1 mM sodium carbonate. The mixture was heated on a water bath at $60°$ C. for 6 hours.

The DMF was evaporated and the remaining solid was dissolved in methanol and filtered. Diluted hydrochloric acid was added to the methanol solution. After two hours at room temperature the solvent was evaporated and G-A-A was obtained. After administering to carnation the compound was found to be an effective means against ageing.

Example 5

Increasing the sensitivity of the plant to PGRs using elicitors

The effect of the elicitors on rooting regeneration on apple stalk slices was studied. The stalk slices were incubated on medium with elicitors in combination with a sub-optimal auxin concentration (1 μM indolebutyric acid or 1 μM indoleacetic acid) which were added for 1 or 3 days to the plant tissue for testing. The increase was measured in the number of regenerated roots compared to the auxin control.

The elicitor uridine was tested on shoot regeneration in saintpaulia, lateral root formation in pea, cell division in tobacco and root induction in larkspur and apple. Table 1 below shows the results.

The table shows that a large number of elicitors bring about a significant increase in the tissue sensitivity to the activity of auxins.

TABLE 1

Effect of elicitors on regeneration

| elicitor | elicitor concentration | increased regeneration in relation to control (auxin alone) |
|---|---|---|
| (A) elicitors formed from degradation of cell structures | | |
| lignin fragments | 0.1 $\mu$M | 400% |
| tannic acid | 1 $\mu$M | 225% |
| jasmonic acid | 0.01 $\mu$M | 210% |
| nonanoic acid | 0.1–1 $\mu$M | 300% |
| uridine (apple stalk slices) | $10^{-10}$ M | 75% |
| uridine (shoot regeneration) | $10^{-10}$ M | 100% |
| uridine (lateral root formation) | $10^{-8}$ to $10^{-16}$ M | 100% |
| uridine (cell division) | $10^{-10}$ M | 75% |
| uridine (root formation larkspur) | $10^{-10}$ M | 50% |
| jasmonic acid linked to indolebutyric acid (without free auxin; rooting of rose) | 0.2% rooting powder | 35% |
| (B) elicitors not formed from degradation of cell structures | | |
| lipo(chito)oligosaccharides (root formation apple) | 0.1 $\mu$M | 350% |
| lipo(chito)oligosaccharides (flower bud formation in tobacco) | 0.1 $\mu$M | 25% |
| fusicocine | 0.01 $\mu$M | 75% |
| pythium extract | 0.01 to 0.1 mg/l | 375% |
| cellulase/pectinase | 0.1 to 1 mg/l | 225% |
| 4-acetamidophenol | 1 $\mu$M | 75% |

Example 6

Linking of an elicitor to a PGR

Indolebutyric acid (I-B-A) was linked to jasmonic acid (I-S-A) essentially with the method given in example 2. I-B-A-J-A was found to be an effective means in root induction in the rose (see table).

Example 7

Examples of synthesized chemically modified AOA's which inhibit the formation of ethylene activity All compounds were tested for their ability to delay flower senescence in carnation and lily.

1. Synthesis of tertiair-butyloxycarbonylaminooxyacetic acid (t-Boc-AOA)

Tertiair-butyloxycarbonyl (t-Boc) and benzyloxycarbonyl are protecting groups for the amino group of AOA (aminooxyacetic acid). This blocks the protonation of the amino group of AOA, which is prerequisite for good transport of the anti-ethylene compound.

The compound was prepared as follows. 18 mmol AOA (aminooxyacetic acid) is dissolved in 30 ml 1 N NaOH. 20 ml of t-butanol is added and the mixture is stirred till a clear solution is obtained. 18.5 mmol di-tert-butyl-dicarbonate is added and the mixture is stirred for another 12 h. The mixture is extracted with pentane (2×50 ml). The combined pentane layers are extracted with saturated $NaHCO_3$ (3×20 ml). All water extracts are combined, acidified with 1.1 M $KHSO_4$ on ice till pH 1 and extracted with ether (5×40 ml). The ether phase is washed with $H_2O$ (2×30 ml) and dried on $Na_2SO_4$. Evaporation of the ether gave t-Boc-AOA (tertiair-butyloxycarbonyl-aminoxyacetic acid).

2. Synthesis of N,N'(di-tertiair-butyloxycarbonylamino-oxyacetic acid) ethylenediamine (t-Boc-AOA-NH-$CH_2$-)$_2$ 2.2 mmol t-Boc-AOA and 2.2 mmol N-methylmorpholine is dissolved in 30 ml THF (tetrahydrofuran). The solution is cooled at 0° C. and 2.2 mmol isobutylchloroformate is added to the stirred solution. After 0.5 h, 1 mmol ethylendiamine is added. After 12 h, the solvent is evaporated and the product is extracted with ethylacetate. Evaporation of the ethylacetate afforded (t-Boc-AOA-NH-$CH_2$-)$_2$.

3. Synthesis of N-N'(di-aminooxyacetic acid) ethylene-diamine (AOA-NH-$CH_2$-)$_2$ 10 mmol (t-Boc-AOA-NH-$CH_2$-)$_2$ is dissolved in 15 ml hydrobromic acid (33 wt. % solution in glacial acetic acid). After 12 h the mixture is poured into 40 ml ether (cold). The precipitate is filtered off and rinsed with another 40 ml ether. After drying pure (AOA-NH-$CH_2$-$_2$ is obtained.

4. Synthesis of benzyloxycarbonyl-AOA

First, a AOA-ethyl ester was synthesised by adding 4 g Thionylchloride to 75 ml ethanol. After 0.5 h, 25 mmol AOA is added (at 0° C.). The mixture is stirred at room temperature for another 12 h. After evaporation of the solvent, the crude product is stripped twice with a small volume of ether. Then, 20 mmol AOA-ethyl ester is dissolved in 40 ml 10% $Na_2CO_3$ at 0° C. 20 mmol benzylchloroformate in 10 ml $CH_2Cl_2$ is dropped slowly (one drop/4 s) to the heavily stirred solution. After 12 h, the mixture is extracted with $CH_2Cl_2$ and after evaporation of the extraction solvent benzyloxycarbonyl-AOA-ethyl ester is obtained. Saponification of the ethyl ester with NaOH gave benzyloxycarbonyl-AOA.

5. Synthesis of propionic-AOA.

30 mmol propionic acid and 33 mmol hydroxysuccinimide is dissolved in 50 ml THF. After 0.5 h, 33 mmol N,N'-dicyclohexylcarbodiimide is added at 0° C. to the stirred solution. After 1 h, 35 mmol AOA-ethyl ester and 35 mmol triethylamine are added (at 0° C.) to the stirred solution and the mixture is stirred further overnight. After evaporation of the THF, the crude product is extracted with ethylacetate. Saponification of the propionic-AOA-ethyl ester gave propionic-AOA.

All compounds did show a significant improvement in the delay of flower senescence when compared to unmodified AOA. In general a lower concentration of the modified compounds could be used to obtain comparable delay.

The compounds as described in examples 2, 4 and 6 have properties similar to the above described AOA's.

Example 8

Chemically modified auxins tested on the rooting of various plants

Attaching IAA to BSA is done to increase the amount of IAA administered to the roots. Up to 32 IAA molecules can be attached to BSA in 2 different ways. Either as N-conjugate of IAA or as C-conjugate. Upon addition of the IAA-BSA to plantroots, the IAA is split off in the root and leads to the availability of IAA during a longer period allowing the root tissue to become sensitive.

1. Synthesis of indoleacetic acid-N-conjugate with BSA (IAA-N-BSA).

500 mg (3 mmol) indole acetic acid was dissolved in 10 ml (end volume) of 0,05 M sodium borate, keeping the pH constant with 1 N KOH. Subsequently, the mixture was neutralized with 1 N HCl. Next, 500 mg (7,5 $\mu$mol) bovine serum albumine was dissolved in 3 ml water and thereafter 3 ml 3M sodiumacetate, 4 ml 7,5% formaldehyde (w/v) and the IAA-solution descibed above were added.

This mixture was incubated at 22° C. (under $N_2$) in the dark under continuous stirring for 13 hours. The mixture was then dialyzed twice for 24 hours against 10 l 0,1 N sodium hydrogencarbonate, followed by five dialyses of 24 hours against 10 l water. Purified IAA-N-BSA was obtained by lyophilizing this solution and was stored at −80° C.

A similar procedure was followed with IBA instead of IAA, resulting in IBA-N-BSA 2. Synthesis of indoleacetic acid-C-conjugate with BSA (IAA-C-BSA)

52 mg (0,3 mmol) IAA and 75 Al (o,3 mmol) tri-n-butylamine are dissolved in 2 ml DMF in a two-tacked round bottom receiver, kept at −15° C. under $N_2$ in dimmed light, under magnetic stirring. This is allowed to cool to −15° C. Then, 40 μl isobutylchlorocarbonate is added an allowed to react for 8 minutes (solution A).

The second part of the synthesis is performed at −4° C. Solution A is added to an ice cooled mixture of i) 121 mg (6,2 μmol) BSA (globulin-free) in 22 ml water/DMF (1 to 1 by volume) and ii) 0,42 ml 1 N NaOH under continuous stirring. After incubation for 1 hour in dimmed light 92 ml 1 N NaOH was added. This reaction mixture was stirred for 5 hours and thereafter dialyzed during 1 day against 2 l 10% DMF in water and thereafter for 4 days against water (in the dark). After freeze drying the purified IAA-C-BSA was stored at −80° C.

IAA-C-BSA is somewhat less effective in root induction as IAA-N-BSA, but still better than IAA alone.

3. Synthesis of 1-N-Indole-3-Hexanoic Acid (IHA)

This compound is an extended form of Indole Butyric Acid (IBA). Both compounds are turned over to IAA and are believed to act through IAA as the active hormone. IBA is the known hormone from nature, which is also commercially available. IHA is synthesised in the same way as IBA.

7,5 g Indole and 6,4 g of powdered 85% KOH are added to 100 ml tetrahydronaphtalene (tetraline) in a round bottom of 250 ml, equipped with a Dean-Stark trap and a condenser. The mixture is heated to 100° C. and 8,4 g ε-caprolactam is added. Subsequently the mixture is heated to 230° C. on a silico oil bath and reacted for 8–16 h under vigourous stirring. After cooling down to room temperature the reaction mixture is extracted with 300 ml water. The water-layer is separated and collected in an erlemeyer flask and cooled down to 0° C. and kept at that temperature during addition of concentrated HCl until a pH of 2–3 is reached. The precipitate is filtered off, dried and recrystalised from methanol. The yield varies from 25% to 75% depending on the reaction conditions. The method described is based on an adjusted form of a synthesis published in J.Organic Chem., vol.28, 1384 (1963).

A comparision between some of the more effective rooting powders is given in Table 2.

In this table standard Indol Butyric Acid (IBA), which is the active component in most currently used rooting powders, is compared with Indol Hexanolic acid (IHA) and two BSA adducts, both N-coupled, namely IBA and indole acetic acid (BSA-N-IAA). The effect on rooting and the plant development (stem growth, outgrowth of new shoots, synchronicity of growth of a population of plants) were inter alia factors determining the place in the categories which ranged from 1 to 6. The compounds with the best relative overall effect on rooting and development were placed in category I. Rooting and subsequent development of scions of different types of herbaceous and woody plants differs largely for those type of plants. A rose cultivar, "enermus stur cinq", was used as an example of a recalcitrant woody plant. The chrysanthemum species "regan" is an example of an easy to root herbaceous plant.

TABLE 2

| species hormone | rose enermus stur cinq | rose n. brier | chrys. regan | chrys. snowdon | carnation tempo | carnation m. brilj. | av. |
|---|---|---|---|---|---|---|---|
| IBA | 3 | 1 | 4 | 1 | n.d. | n.d. | 2.25 |
| IHA | 1 | 1 | 2 | 1 | 2 | 1 | 1.33 |
| BSA-N-IBA | 2 | 1 | 4 | 1 | 3 | 1 | 2.0 |
| BSA-N-IAA | 1 | 3 | 1 | 2 | 3 | 1 | 1.8 |

From the table it is apparent that IHA is very general applicable and very effective. The IAA-variant of BSA is somewhat more effective than the IBA-variant. BSA-N-IAA seems to be especially suited for recalcitrant plants. In apple IAA may induce a maximum of 3,5 roots per tissue fragment, while IAA-N-BSA induces a maximum of 8 roots per tissue fragment. Very recalcitrant trees like summer oak and cork oat can be rooted to a much higher percentage than with any of the conventionally applied rooting powders. The compounds described in example 3 and together with elicitors in Table 1 show similar effects. The concentration needed to obtain maximal root formation is in all synthesized compounds significant lower than either IAA or IBA.

Example 9

Modified IBA for improved rooting

The auxin compounds were tested with respect to rooting in apple and rose.

1. Synthesis of IBA-AIB

Indolebutyric acid (IBA) was coupled to amino-isobutyric acid (AI). AIB is an anti-ethylene compound that counteracts the ethylene-induced inhibition of auxin action (ethylene inhibits rooting). Due to the chemical modification the activity of both IBA and AIB are increased. The combination of IBA and AIB proved to be more active than the standard hormone treatment.

5 mmol isobutyl chloroformate is added to a cooled solution (−10° C.) of 5 mmol indole butyric acid (IBA) and 5 mmol N-methylmorpholine in 30 ml THF. After stirring for half an hour a solution of 5 mmol amino isobutyric acid ethyl ester (AIBOEt) and 5 mmol triethylamine in 20 ml THF is added. The reaction mixture is stirred for another two hours at −10° C. and 40 hours at ambient temperature. After filtration and evaporation of the reaction mixture the residue is dissolved in 50 ml ethylacetate (EtOAc) and washed twice with 1 N HCl solution (2×40 ml), twice with 5% (w/w) $NaHCO_3$ solution (2×40 ml) and once with saturated NaCl solution, dried over anhydrous $Na_2SO_4$, filtered and evaporated to yield IBA-AIBOEt.

Saponification of IBA-AIBOEt in MeOH with 1 N NaOH gave after acidification with 1 N HCl at 0° C. and recrystalization at least 99% pure free acid IBA-AIB.

2. Synthesis of IBA-Gly-AIB

IBA-Gly-AIB was synthesized by the same procedure as described above by using Gly-AIBOEt instead of AIBOEt.

Tests are performed by the stem-disk method as published by Van der Krieken et al., Plant Cell Reports (1993), vol. 12, 203–206, in which the number of roots of a large number of stem-disks cut from a particular plant are counted and treated with rooting powder containing in this case the compounds described. The results with this compound on rooting of tissue was also much better then with IBA alone.

Example 10

Modified NAA for fruit-thinning

Naphtalene acetic acid (NAA) is a well known compound applied for the thinning of fruit. The drawback of NAA is the fact that the compound is only effective in a very narrow concentration range. Spraying and humidity can be of crucial importance to the effectiveness of the treatment.

Two compounds were synthesized to test the general observation made by us, namely that chemically modified PGRs are effective over a much larger concentration range than the unmodified PGRs, especially when combined with an elicitor. This means that modified NAA should work over a much broader concentration range than NAA itself.

The two compounds tested on a total of 40 trees were Naphtyl Acetic Anhydride (NAA) and Naphtyl Acetic Acid-aceetamide Naftyl (2 NA's coupled by a peptide bond).

Two different cultivars of apple and one cultivar of pear were sprayed with three different concentrations of the respective compounds. Initial observations do indicate that both compounds are effective in thinning and work over a larger concentration range.

What is claimed is:

1. Method for increasing and/or prolonging in vivo or in vitro activity of plant growth regulators (PGRs), comprising:
   a) increasing the sensitivity of the plant and/or plant part(s) to the activity of plant growth regulators by administration or application of one or more means which result in a defensive response in the plant; and
   b) along with or after the administration or application of the one or more means which result in a defensive response in the plants, locally increasing the concentration of active plant growth regulators in a plant and/or plant part(s) by either or both of the following:
      i) administering the PGR(s) in encapsulated form; or
      ii) administering PGR(s) that have been chemically modified by linking it (them) to one or more carrier molecules, optionally with interposing of a spacer molecule.

2. Method as claimed in claim 1, characterized in that the one or more carrier molecules are linked to the PGR(s) in enzymatically degradable manner.

3. Method as claimed in claim 1, characterized in that the carrier molecules are transportable compounds selected from the group consisting of carbohydrates, sterols, terpenes, and phosphorylated hydrocarbons, optionally linked to the PGR with interposing of a spacer molecule.

4. Method as claimed in claim 1, 2 or 3, characterized in that the carrier molecules are compounds which are linked to a group on the PGR which is involved in metabolic degradation of the PGR in order to prevent this degradation.

5. Method as claimed in claim 1, characterized in that the chemical modification of the PGR(s) consists of neutralizing the polarity of the PGR(s) by linking to the PGR at least one carrier molecule, spacer molecule or a second PGR to cause the polarity to disappear.

6. Method as claimed in claim 1, characterized in that the chemical modification of the PGR(s) consists of increasing the polarity of the PGR by linking to the PGR a very charged molecule.

7. Method as claimed in claim 4, characterized in that the compounds protecting against degradation also serve as spacer molecules and are selected from the group consisting of succinic acid, malonic acid, and diaminoalkanes.

8. Method as claimed in claim 1, characterized in that the means which result in a defensive response are elicitors selected from the group consisting of oligosaccharides, lignin fragments, tannic acid, jasmonic acid, nonanoic acid, uridine, lipo-chito-oligosaccharides, fusicoccine, pythium extract, and 4-acetamidophenol.

9. Method as claimed in claim 1, characterized in that the means which result in a defensive response are means which induce the release of elicitors selected from the group consisting of pectinase, glucanase, cellulase, UV-B, and ozone.

10. Method as claimed in claim 1, characterized in that the means which result in a defensive response are intermediaries from the phytoalexin biosynthesis.

11. Method as claimed in claim 1, characterized in that the means which result in a defensive response are formed by gene(s) introduced into the plant which code(s) for elicitors or for enzymes which result in an increase of the concentration of elicitors.

12. Method as claimed in claim 11, wherein the gene is a NOD gene of *Rhizobium*.

13. The method of claim 1 in which the PGR is tertiary-butyloxycarbonylaminooxyacetic acid.

14. Method for increasing and/or prolonging in vivo or in vitro activity of plant growth regulators (PGRs), comprising first administering one or more elicitors to a plant or plant tissue, allowing enough time to pass to enable the elicitors to sensitise the plant or plant tissue to the action of one or more PGRs and then administering one or more chemically modified PGRs consisting of at least one PGR which is linked to at least one carrier molecule, with the proviso that if the carrier molecule is a sugar molecule a spacer is interposed in between the PGR and the carrier molecule.

15. Method for increasing and/or prolonging in vivo or in vitro activity of plant growth regulators (PGRs), comprising the simultaneous administration to a plant or plant tissue of one or more elicitors and one or more slow-release PGRs consisting of at least one PGR which is linked to at least one carrier molecule, with the proviso that if the carrier molecule is a sugar molecule a spacer is interposed in between the PGR and the carrier molecule.

* * * * *

UNITED STATES PATENT AND TRADEMARK OFFICE
CERTIFICATE OF CORRECTION

| | | |
|---|---|---|
| PATENT NO. | : 6,242,381 B1 | Page 1 of 1 |
| DATED | : June 5, 2001 | |
| INVENTOR(S) | : Wilhelmus M. Van der Krieken et al. | |

It is certified that error appears in the above-identified patent and that said Letters Patent is hereby corrected as shown below:

Title page,
Item [73] Assignee, after "(NL)" insert -- Seed Capital Investments-2 (SCI-2) B.V. (NL) --.

Signed and Sealed this

Eighteenth Day of December, 2001

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,242,381 B1
DATED : June 5, 2001
INVENTOR(S) : Wilhelmus Maria Van der Krieken et al.

It is certified that error appears in the above-identified patent and that said Letters Patent is hereby corrected as shown below:

Column 2,
Line 45, "PGRS" should read -- PGRs --.

Column 3,
Line 11, "PGR's" should read -- PGRs --.

Column 11,
Line 13, "75 Al" should read -- 75 µl --.
Line 19, "-4°C" should read -- 4°C -- (delete negative).

Column 13, claim 4,
Line 52, "as claimed in claim 1, 2 or 3" should read -- as claimed in claim 1 --.

Signed and Sealed this

Second Day of April, 2002

Attest:

Attesting Officer

JAMES E. ROGAN
Director of the United States Patent and Trademark Office